(12) United States Patent
Cannon

(10) Patent No.: US 7,230,712 B2
(45) Date of Patent: Jun. 12, 2007

(54) REDUCTION OF RESIDUAL AMPLITUDE MODULATION IN FREQUENCY-MODULATED SIGNALS

(75) Inventor: Bret D. Cannon, Richland, WA (US)

(73) Assignee: Battelle Memorial Institute, Richland, WA (US)

(*) Notice: Subject to any disclaimer, the term of this patent is extended or adjusted under 35 U.S.C. 154(b) by 297 days.

(21) Appl. No.: 10/700,161

(22) Filed: Nov. 3, 2003

(65) Prior Publication Data

US 2005/0094149 A1    May 5, 2005

(51) Int. Cl.
  *G01N 21/00* (2006.01)
(52) U.S. Cl. ...................................... 356/437
(58) Field of Classification Search ............ None
  See application file for complete search history.

(56) References Cited

U.S. PATENT DOCUMENTS

| | | | |
|---|---|---|---|
| 4,034,285 A | 7/1977 | Ashley et al. |
| 4,305,666 A | 12/1981 | Becherer et al. |
| 4,398,293 A | 8/1983 | Hall et al. |
| 4,523,847 A | 6/1985 | Bjorklund et al. |
| 4,590,597 A | 5/1986 | Long-sheng et al. |
| 4,594,511 A | 6/1986 | Cooper et al. |
| 4,856,009 A | 8/1989 | Hall et al. |
| 4,856,899 A | 8/1989 | Iwaoka et al. |
| 4,905,244 A | 2/1990 | Wyeth et al. |
| 5,070,260 A | 12/1991 | Wong |
| 5,267,019 A | 11/1993 | Whittaker et al. |
| 5,285,308 A | 2/1994 | Jenkins et al. |
| 5,293,213 A | 3/1994 | Klein et al. |
| 5,317,156 A | 5/1994 | Cooper et al. |
| 5,339,177 A | 8/1994 | Jenkins et al. |
| 5,347,392 A | 9/1994 | Chen et al. |
| 5,441,054 A | 8/1995 | Tsuchiya |

(Continued)

FOREIGN PATENT DOCUMENTS

EP    0 373 945 B1    2/1994

(Continued)

OTHER PUBLICATIONS

*Stabilization and Frequency Measurement of the $I_2$-Stabilized Nd: YAG Laser*, Hall, Ma, Taubman, Tiemann, Hong, Pfister and Ye, IEEE Transactions on Instrumentation and Measurement, vol. 48, pp. 583-586 (Apr. 1999).

(Continued)

*Primary Examiner*—Michael P. Stafira
(74) *Attorney, Agent, or Firm*—Klarquist Sparkman, LLP

(57) ABSTRACT

One system of the present invention includes a modulated light source subsystem to provide a first light signal with a first modulation index, and a second light signal with a second modulation index. The system also includes a region to receive an analyte for evaluation and direct the first light signal thereto, and a detector responsive to the second light signal and a third light signal from the region to provide an output representative of spectroscopic information. The third light signal further includes noise induced by residual amplitude modulation that is reduced at the detector by the second light signal in accordance with a difference between the first modulation index and the second modulation index.

25 Claims, 6 Drawing Sheets

U.S. PATENT DOCUMENTS

| | | | |
|---|---|---|---|
| 5,477,368 A * | 12/1995 | Eskildsen et al. | 398/147 |
| 5,502,562 A | 3/1996 | Werle | |
| 5,566,381 A | 10/1996 | Korotky | |
| 5,636,035 A * | 6/1997 | Whittaker et al. | 356/437 |
| 5,644,123 A | 7/1997 | Hait | |
| 5,771,255 A | 6/1998 | Horiuchi et al. | |
| 6,094,267 A | 7/2000 | Levenson et al. | |
| 6,356,350 B1 * | 3/2002 | Silver et al. | 356/437 |
| 6,400,449 B2 * | 6/2002 | Maris et al. | 356/72 |
| 6,483,582 B2 | 11/2002 | Modlin et al. | |
| 2002/0093716 A1 | 7/2002 | Hiraizumi | |

FOREIGN PATENT DOCUMENTS

| | | |
|---|---|---|
| EP | 0 720 313 B1 | 6/1999 |

OTHER PUBLICATIONS

*Frequency locking to a high-finesse Fabry-Perot cavity of a frequency doubles Nd:YAG laser used as the optical phase modulator*, Bregant, Cantatore, Valle, Ruoso, Zavattini (Feb. 28, 2002).

*Analysis of Cleaved Coupled-Cavity ($C^3$) Diode Lasers-Part II: Frequency Modulation, Above Threshold Operation, and Residual Amplitude Modulation**, Streifer, Yevick, Paoli and Burnham, IEEE Journal of Quantum Electronics vol. QE-21, pp. 539-550 (Jun. 1985).

*Low-amplitude-noise laser for AURIGA detector optical readout*, Conti, DeRose, Marin, Applied Optics, vol. 39, pp. 5732-5738 (Nov. 2000).

*Progress Report on the Laser Absorption Spectrometer Development*, Spiers, Menzies, Philips, Ransom, no date.

*Optical interference fringe reduction in frequency-modulation spectroscopy experiments*, Hjelme, Neegard, Vartdal, Optical Society of America, pp. 1731-1733 (Mar. 17, 1995).

*Modulation transfer processes in optical heterodyne saturation spectroscopy*, Shirley, Optical Society of America, pp. 537-539 (Jul. 9, 1982).

*Opitcal Heterodyne Spectroscopy Enhanced by an External Optical Cavity: Toward Improved Working Standards*, IEEE Journal of Quantum Electronics, vol. 26, pp. 2006-2012 (Nov. 1990).

*Residual amplitude modulation in laser electro-optical phase modulation*, Whittaker, Gehrtz, Bjorklund, J. Opt. Soc. Am. B, vol. 2, pp. 1320-1326 (Aug. 1985).

* cited by examiner

REDUCTION OF RESIDUAL AMPLITUDE MODULATION IN FREQUENCY-MODULATED SIGNALS

GOVERNMENT RIGHTS

This invention was made with Government support under Contract Number DE-AC0676RLO1831. The Government has certain rights in the invention.

BACKGROUND

The present application relates to the reduction of undesired amplitude modulation, and more particularly, but not exclusively, relates to the reduction of residual amplitude modulation in frequency-modulated signals carrying information.

Various techniques for detecting extremely low concentrations of a substance of interest have been developed that involve Frequency Modulation (FM) of a laser beam. These techniques include Frequency Modulation Spectroscopy (FMS), wideband FM, Wavelength Modulation Spectroscopy (WMS), and the like. Generally, the frequency-modulated laser light is directed through an analyte that is characterized by spectral absorption and/or dispersion of the interrogating light. The returned light, an altered form of the interrogating light, is detected and evaluated to determine these spectroscopic characteristics of interest. More particularly, FMS can utilize a one-tone modulation technique or a two-tone modulation technique as is further explained in the article by Silver, Joel A., *Frequency-Modulation Spectroscopy for Trace Species Detection: Theory and Comparison Among Experimental Methods*, APPLIED OPTICS, Vol. 31, No. 6 (20 Feb. 1992), which is hereby incorporated by reference.

Frequency modulation of laser light typically results in an undesired amount of Amplitude Modulation (AM), so-called Residual Amplitude Modulation (RAM), due to nonideal behavior of the laser and/or other elements of the system. Unfortunately, residual amplitude modulation limits the sensitivity of FM techniques with lasers—functioning as a form of noise that can at least partially obscure spectroscopic information in the output signal.

One scheme to reduce residual amplitude modulation depends on frequency modulation of the laser beam with an Electro-Optic Modulator (EOM). Unfortunately, the frequency modulation index range available with existing EOMs is somewhat limited—such that very high modulation frequencies are needed—correspondingly increasing cost and complexity of the system. Furthermore, suitable EOMs are not available for certain interrogation wavelength ranges that have promising applications.

In principle, it has been recognized that residual amplitude modulation can be avoided by detecting an absorption signal in a phase-sensitive manner when the phase of the residual amplitude modulation is different from the phase of the frequency modulation signal. Generally, it is optimal that this phase difference be 90°. However, this scheme is also limited by very stringent requirements regarding linearity and dynamic range of various system elements. Furthermore, phase of the residual amplitude modulation needs to remain stable for such schemes to be effective.

Still another scheme exists peculiar to lead-salt lasers. For this scheme, the laser is operated at or near an operational limit for which laser output power is generally independent of electric current. Drawbacks of this approach include a limited availability of wavelengths for absorption detection and the adverse impact such operation has on the lifetime of the laser.

Accordingly, there is a need for further contributions in this area of technology.

SUMMARY

One embodiment of the present invention is a unique technique for reducing unwanted amplitude modulation. Other embodiments include unique systems, devices, apparatus, and methods for reducing residual amplitude modulation of frequency-modulated signals.

A further embodiment of the present invention includes providing a first light signal that is frequency-modulated with a first modulation index and a second light signal that is frequency-modulated with a second modulation index; controlling a difference between the first modulation index and the second modulation index; and combining the first light signal and second light signal to reduce residual amplitude modulation in accordance with this difference. In one form, the first light signal and the second light signal are frequency-modulated at the same frequency, and the carrier frequency from one to the other is shifted by a predefined amount.

Another embodiment of the present invention includes: providing frequency-modulated light carrying information that is at least partially concealed by undesired amplitude modulation and has a first modulation index; generating other light that is frequency-modulated with a second modulation index and a different carrier frequency; and at least partially nulling the undesired amplitude modulation with the other light to improve detection of the information. In one form, this information may be spectroscopic in nature.

Still another embodiment of the present invention includes a modulated light subsystem to provide a first frequency-modulated light signal with a first modulation index and a second frequency-modulated light signal with a second modulation index, an analyte interrogation region, a feedback device, and a detector. The second light signal has a carrier frequency different than the first light signal. In the interrogation region, the first light signal is directed to an analyte to provide a third frequency-modulated light signal including spectroscopic information about the analyte with residual amplitude modulation. The feedback device is responsive to the first light signal and second light signal to control a difference between the first and second modulation indices, and the detector is responsive to the second light signal and third light signal to provide an output corresponding to the spectroscopic information with the residual amplitude modulation reduced in accordance with the modulation index difference.

Yet another embodiment of the present invention includes means for interrogating a material to provide a first frequency-modulated light signal having a first modulation index that carries spectroscopic information with residual amplitude modulation, means for generating a second frequency-modulated light having a second modulation index, and means for reducing the residual amplitude modulation in accordance with the difference between the first and second modulation indices to improve detection of the spectroscopic information.

Accordingly, one object of the present invention is to provide a unique technique for reducing undesired amplitude modulation.

Another object is to provide a unique system, method, device, or apparatus for reducing residual amplitude modulation of frequency-modulated signals.

Other objects, embodiments, forms, features, advantages, aspects and benefits of the present invention shall become apparent from the detailed description and drawings included herein.

DETAILED DESCRIPTION

Figure 1:
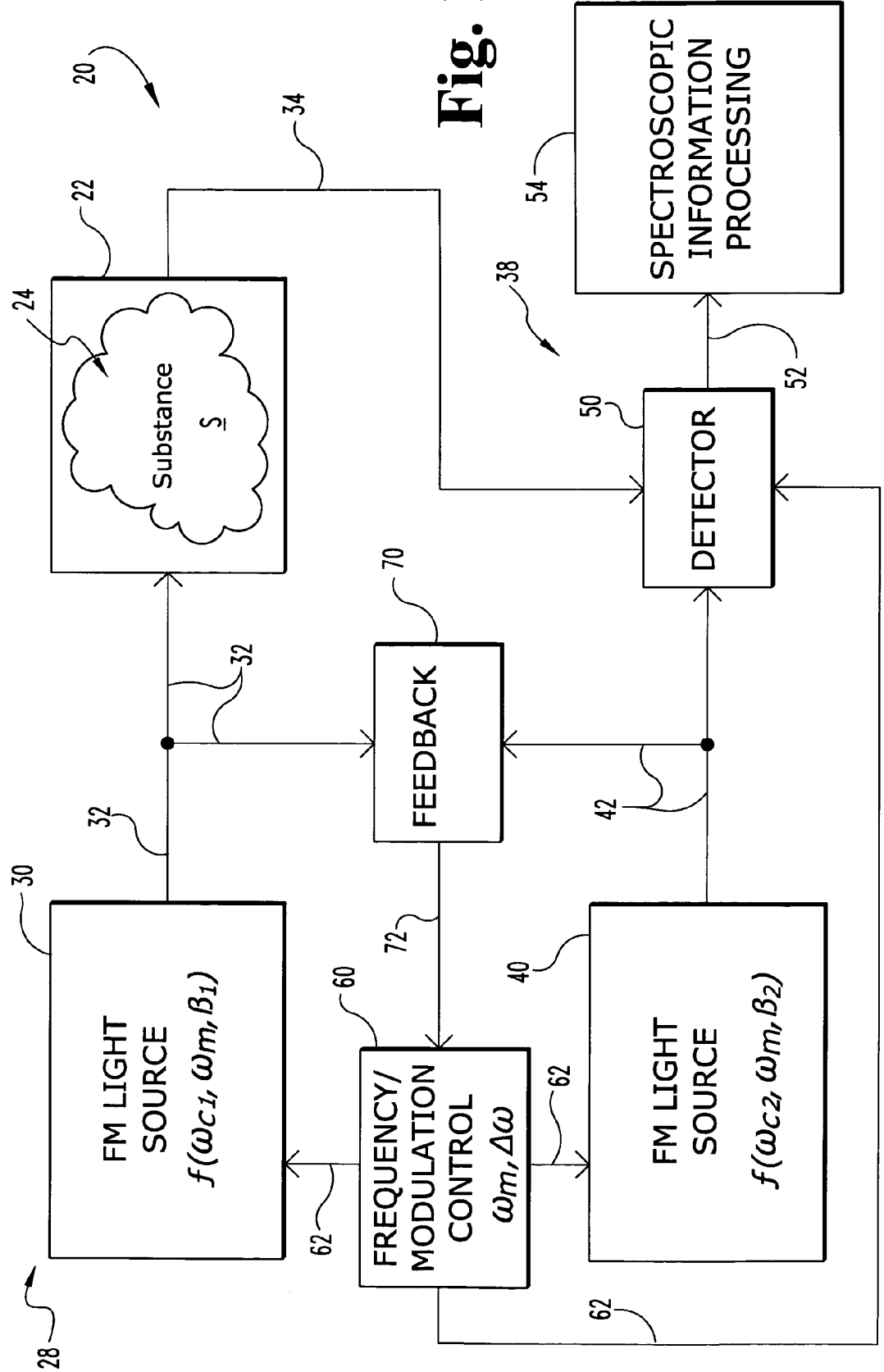
FIG. 1 is a generalized signal diagram of an evaluation system according to the present invention.

While the present invention may be embodied in many different forms, for the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Referring now to FIG. 1 spectroscopic evaluation system 20 is depicted. System 20 is operable to spectroscopically determine concentration, identity, and/or one or more other characteristics of substance S. Substance S is typically in a gaseous form contained in sample cell 22 of evaluation region 24. System 20 further includes modulated light source subsystem 28, detection subsystem 38, and feedback subsystem 70. Subsystem 28 includes frequency-modulated light source 30 and frequency-modulated light source 40. Sources 30 and 40 are typically of a variety operable to provide a desired wavelength ($\lambda$) output that can be scanned over a desired range and with a desired degree of coherency. In one form, sources 30 and 40 are of a diode laser or quantum cascade laser type that are modulated by varying electric drive current. In another form, a lead-salt laser is utilized. In still other forms, source 30 and/or 40 is a different type as would occur to those skilled in the art.

Frequency-modulated light source 30 produces interrogation light signal 32 with a modulation frequency $\omega_m$, carrier frequency $\omega_{c1}$, and modulation index $\beta_1$. Interrogation light signal 32 is transmitted to evaluation region 24 and feedback subsystem 70. Interrogation light signal 32 impinges on substance S in evaluation region 24, at least a portion of which passes through or is returned by substance S as return/response light signal 34. Return/response light signal 34 can be considered a modified form of interrogation signal 32, being selectively changed due to absorption and/or dispersion by substance S in evaluation region 24. Detection subsystem 38 receives return/response light signal 34.

Frequency-modulated light source 40 transmits correction light signal 42, with modulation frequency $\omega_m$, carrier frequency $\omega_{c2}$, and modulation index $\beta_2$. Correction signal 42 is transmitted to both detection subsystem 38 and feedback subsystem 70.

Subsystem 28 further includes frequency reference and control device(s) 60 to provide appropriate reference frequencies, regulators, amplifiers, modulators, and/or other components to modulate sources 30 and 40 at $\omega_m$ with different center or carrier frequencies $\omega_{c1}$, and $\omega_{c2}$, and different modulation indices $\beta_1$ and $\beta_2$, respectively. Accordingly, device(s) 60 are connected by a number of signal transmission links 62 to transmit various control signals. Feedback subsystem 70 is responsive to interrogation light signal 32 and correction light signal 42 to generate feedback signal 72. Feedback subsystem 70 transmits feedback signal 72 to device(s) 60 to regulate the modulation index difference, which is designated $\Delta\beta$ (where: $\Delta\beta = \beta_2 - \beta_1$) Feedback subsystem 70 can optionally regulate the difference between carrier frequencies, which is designated $\Delta\omega$ (where: $\Delta\omega = \omega_{c2} - \omega_{c1}$).

Detection subsystem 38 includes light detector 50 and spectroscopic information processing device(s) 54. Detector 50 senses a combination of return/response light signal 34 and correction light signal 42. The RAM signal of at least one beat frequency between the return/response light signal 34 and the correction light signal 42 is reduced, if not effectively eliminated while preserving the information about substance S, as is more fully described hereinafter. Detector 50 also receives a control signal via one or more of links 62 to extract (demodulate) spectroscopic information from this combination, and generate a corresponding detector signal 52. This control signal is utilized by subsystem 38 to detect the spectroscopic information in the frequency modulated waveform using standard techniques. Detector 50 can be of any suitable type, such as a photodiode or photomultiplier tube, just to name a couple of examples. Device(s) 54 process detector signal 52 to further analyze, store, output, display, indicate, and/or transmit the spectroscopic information determined from signal 52, if/as desired.

Referring generally to system 20 of FIG. 1, it has been discovered that the interference due to Residual Amplitude Modulation (RAM) intrinsic to sources 30 and 40 can be reduced, if not effectively eliminated, by controlling $\Delta\beta$. Specifically, for selected values of $\Delta\beta$, RAM interference can be essentially nulled-out of a chosen beat frequency between return/response signal 34 and light correction signal 42 to increase sensitivity with respect to information that is otherwise obscured by RAM. Letting $E_1(t)$ represent FM-modulated light signal 32 with RAM, it can be modeled according to expression (a) as follows:

$$E_1(t) = E_1[1 + M_1(\sin(\omega_m \tau + \Psi_1))] * \exp[i\omega_{c1} t + i\beta_1 \sin(\omega_m t)] \qquad (a)$$

where: t represents time, i represents an imaginary number unit, $E_1$ represents electric field magnitude, $\omega_{c1}$ represents carrier frequency, $M_1$ represents RAM magnitude, $\psi_1$ represents phase shift of RAM, $\beta_1$ represents modulation index, and $\omega_m$ represents modulation frequency as previously designated for signals 32 and 42. It should be appreciated that the modulation index $\beta_1$ corresponds to the depth of phase modulation, such that the maximum excursion in frequency from $\omega_c$ is $\beta_1 \omega_m$. To express equation (a) as a summation over Bessel functions, the following expressions (b)–(e) are defined:

$$a_O = -(M_1/2i) * \exp(-i\psi_1); \quad \text{(b)}$$

$$a_1 = 1 \quad \text{(c)}$$

$$a_2 = (M_1/2i) * \exp(i\psi_1); \quad \text{(d)}$$

$$r_1(s, \beta_1) = -a_O J1(\beta_1) + a_1 J0(\beta_1) + a_2 J1(\beta_1) \text{ if } s = 0; \quad \text{(e)}$$

$$= \sum_{k=0}^{2} a_k (-1)^{[-s+(k-1)]} * Jn[-s+(k-1), \beta_1] \text{ if } s < 0;$$

$$= \sum_{k=o}^{2} a_k Jn[s-(k-1), \beta_1] \text{ if } s > 0.$$

where: $a_0$, $a_1$, and $a_2$, represent frequency expansion coefficients; $Jn(s, \beta_1)$ represents a Bessel function of order s at the point $\beta_1$ (note the identity: $Jn(s, \beta_1)=(-1)^s Jn(-s, \beta_1)$ is utiliz respect to the s<0 equation); and k is a summation index. Utilizing expressions (b)–(e), $E_1(t)$ can be written as expression (f) as follows:

$$E_1(t) = E_1 \cdot \exp(i\omega_{c1} t) \cdot \sum_{s=-\infty}^{\infty} r_1(s, \beta_1) \exp(i \cdot s \cdot \omega_m \cdot t) \quad \text{(f)}$$

Representing signal 42 by $E_2(t)$, $E_2(t)$ can be approximated by expression (g) as follows:

$$E_2(t) = E_2 \cdot \exp(i \cdot (\omega_{c1} + \Delta\omega) \cdot t) \sum_{s=-\infty}^{\infty} r_2(s, \beta_2) \exp(i \cdot s \cdot \omega_m \cdot t) \quad \text{(g)}$$

where: $\Delta\beta=(\beta_2-\beta_1)$; $\Delta\omega=(\omega_2-\omega_1)$; $E_2$ represents electric field magnitud determined in a manner analogous to $r_1(s, \beta_1)$. In the absence of wavelength dependent absorption and dispersion, signal 34 returned by substance S, designated $E_{sig}(t, \phi_0)$, is given by expression (h) as follows:

$$E_{sig}(t, \phi_0) = \sqrt{RET} \Bigg( E_1 \cdot \exp(i \cdot \omega_{c1} \cdot t) \cdot \sum_{s=-\infty}^{\infty} r_1(s, \beta_1) \cdot \quad \text{(h)}$$

$$\exp(i \cdot s \cdot \omega_m \cdot t) \cdot \exp\left(\frac{-\alpha(s)}{2} - i\phi(\phi_0, s)\right) \Bigg)$$

where: RET represents returned power fraction, $\alpha(s)$ represents an intensity attenuation (absorption) coefficient at sideband s; $\phi(s)$ represents dispersion at sideband s, $\phi_0$ represents dispersion at carrier frequency $\omega_{c1}$. It should be appreciated that $\phi_0$ is presumed to be between 0 and $2\pi$ because a change in roundtrip pathlength (2d) of the signal by wavelength $\lambda$ changes phase by $2\pi$. Accordingly, $\phi(\phi_0, s)=\phi_0+s\cdot\delta\phi$; where $\delta\phi_0$ represents phase shift between adjacent sidebands.

The intensity of the combined signals 34 and 42 at detector 50, designated $I_{det}$, is represented by expression (i) as follows:

$$I_{det}(t, \phi) = \frac{c^* \varepsilon_0}{2} [(|E_2(t)|)^2 + \quad \text{(i)}$$

$$E_2(t)^* \overline{E_{Sig}(t, \phi_0)} + \overline{E_2(t)}^* E_{Sig}(t, \phi_0) + |E_{Sig}(t, \phi_0)|^2]$$

where: c represents the speed of light, $\epsilon_0$ represents permittivity, and the overbar operator represents the complex conjugate operation. The first squared term of expression (i) corresponds to the component contributed solely by signal 42 and the last squared term of expression (i) corresponds to the component contributed solely by signal 32. The heterodyne term of expression (i) is represented by the sum between the squared terms. The squared terms create detector signals at baseband (DC and low frequencies), at $\omega_m$, and at $2\cdot\omega_m$ and create noise at these frequencies as well as broadband shot-noise. Only the broadband noise will be significant at the frequency used to extract the information about substance S on signal 34 from the heterodyne term if this frequency is well separated from baseband, $\omega_m$, and $2\cdot\omega_m$. From this heterodyne term, the background at the frequency $\Delta\omega$ in the absence of absorption and dispersion can be represented by expression (j) as follows:

$$2E_1 \cdot E_{trans} \cdot \sqrt{RET} \quad \text{(j)}$$

$$\exp\left(\frac{-\alpha_0^{2d}}{2}\right) \cdot \text{Re}\left(\exp(i\Delta\omega t + i\phi_0) \cdot \sum_{s=-\infty}^{\infty} r_2(s, \beta_2) \overline{r_1(s, \beta_1)}\right)$$

For $\beta_2-\beta_1=\Delta\beta$, the following expression (k) represents the term inside the summation operator of expression (j):

$$\text{Back}(\Delta\beta) := \sum_{kp=0}^{2} \sum_{k=0}^{2} b_k^* \overline{a_{kp}^*} Jn(kp-k, \Delta\beta) \quad \text{(k)}$$

Figure 5:
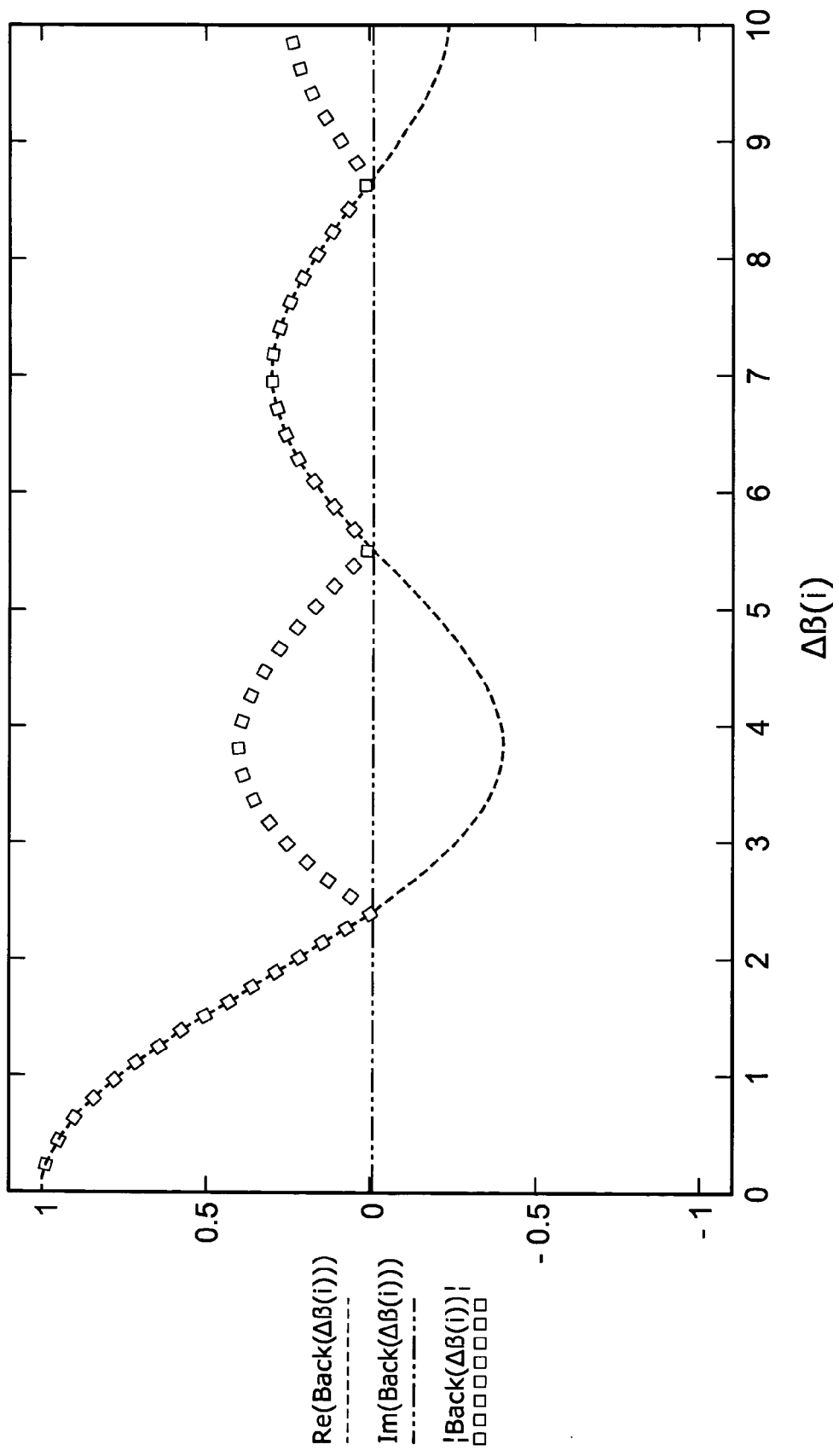
FIGS. 5 and 6 are graphs demonstrating certain aspects of the present invention.

A plot of expression (k) demonstrates that the background (including RAM) can be nulled out for selected values of $\Delta\beta$. FIG. 5 depicts this result as a plot of the real part, the imaginary part and the magnitude of Back($\Delta\beta$) versus $\Delta\beta$ generated utilizing MathCad simulation software (MathCad is supplied by Mathsoft Engineering & Education, Inc. with a business address of 101 Main Street, Cambridge, Mass. 02142-1521) with the following parameters:

$$\varepsilon_0 = 8.854187817 \cdot 10^{-12} \cdot \frac{\text{farad}}{m};$$

$$c = 299792456 \cdot \frac{m}{\text{sec}};$$

$$E_0 = 1 \cdot \frac{\text{volt}}{\text{cm}};$$

$$E_{trans} := 10^2 \cdot \frac{\text{volt}}{\text{cm}};$$

$$\text{Irradiance} = (|E_1|)^2 \cdot \frac{c \cdot \varepsilon_0}{2} = 1.327 \times 10^{-3} \text{ Watt/Cm}^2;$$

$$(|E_{trans}|)^2 \cdot \frac{c \cdot \varepsilon 0}{2} = 13.272 \frac{\text{watt}}{\text{cm}^2};$$

$$\omega_{c1} = 2 \cdot \pi \cdot 30000 \cdot \text{MHz};$$

$$\omega_m = -2 \cdot \pi \cdot 15 \cdot \text{MHz};$$

$$\Delta\omega = 2 \cdot \pi \cdot 2 \cdot \text{MHz};$$

$$\beta_1 = 1;$$

$$n = 1;$$

$$M_1 = 0.05;$$

$$\Psi_1 = \Psi_2 = \pi/2;$$

-continued $M_1 = 0.06$;

$d = 3$ km;

$D = 10$ cm;

$\lambda = 10 \times 10^{-6} m$;

$\alpha_0 = (23.\text{km})^{-1}$;

$dnd\omega = 2.477 \times 10^{-22}$ sec;

$\delta\phi = 8.803 \times 10^{-5}$;

$RET = 6.944 \times 10^{-12}$; and $\phi_0 = 2\pi^*\text{round}(1)$.

Figure 2:
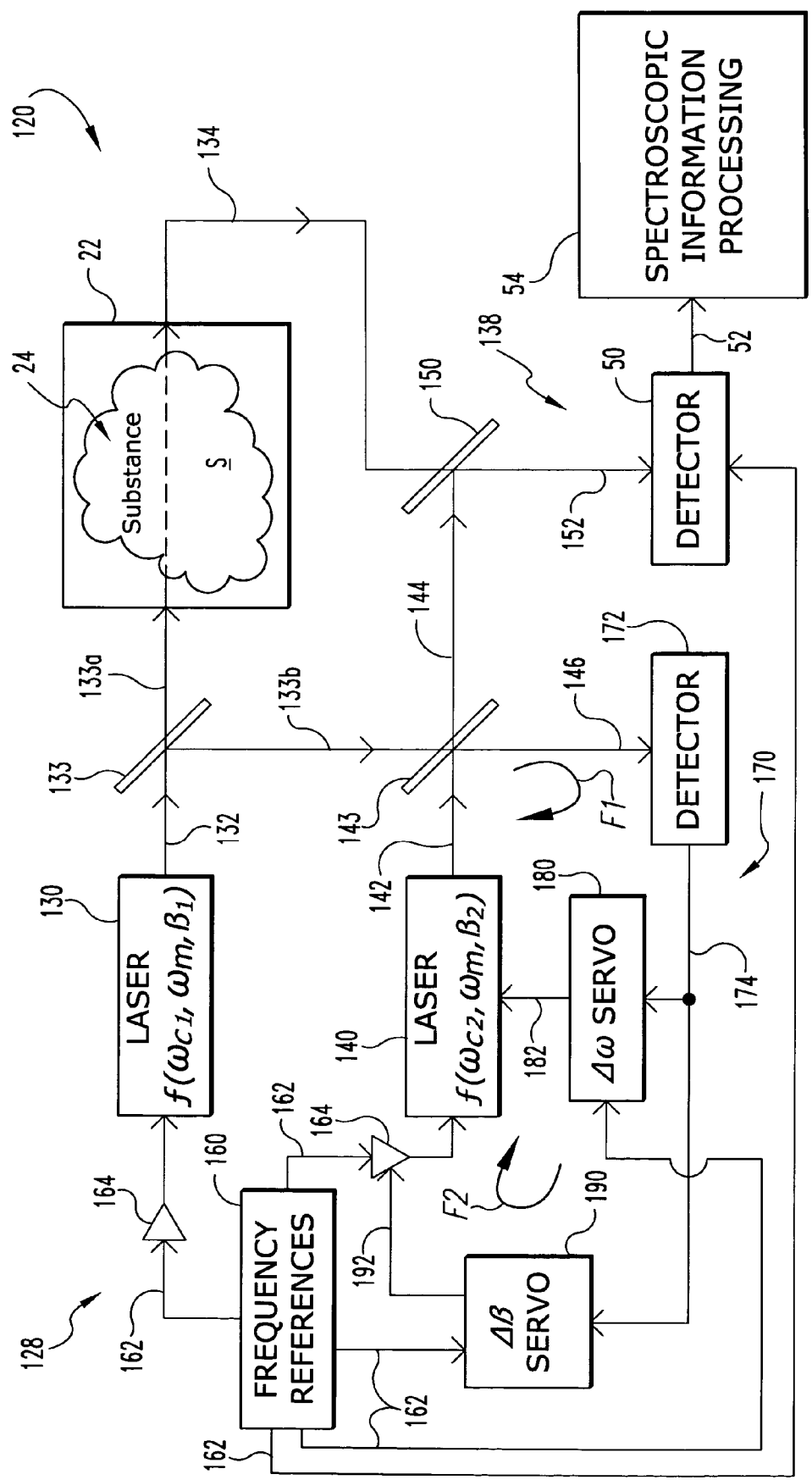
FIG. 2 is a diagrammatic view of a first implementation of the system of FIG. 1.
Figure 3:
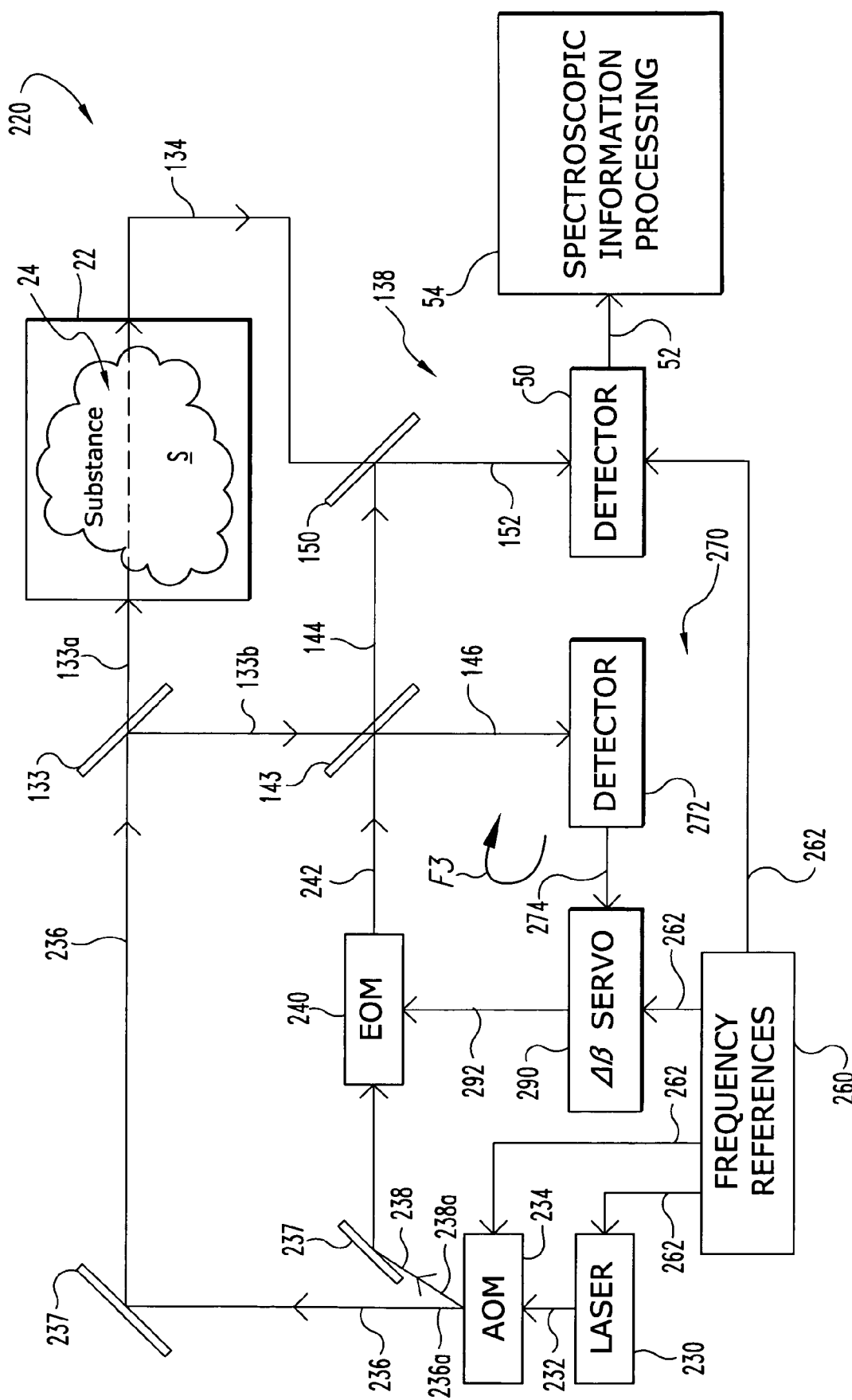
FIG. 3 is a diagrammatic view of a second implementation of the system of FIG. 1.
Figure 4:
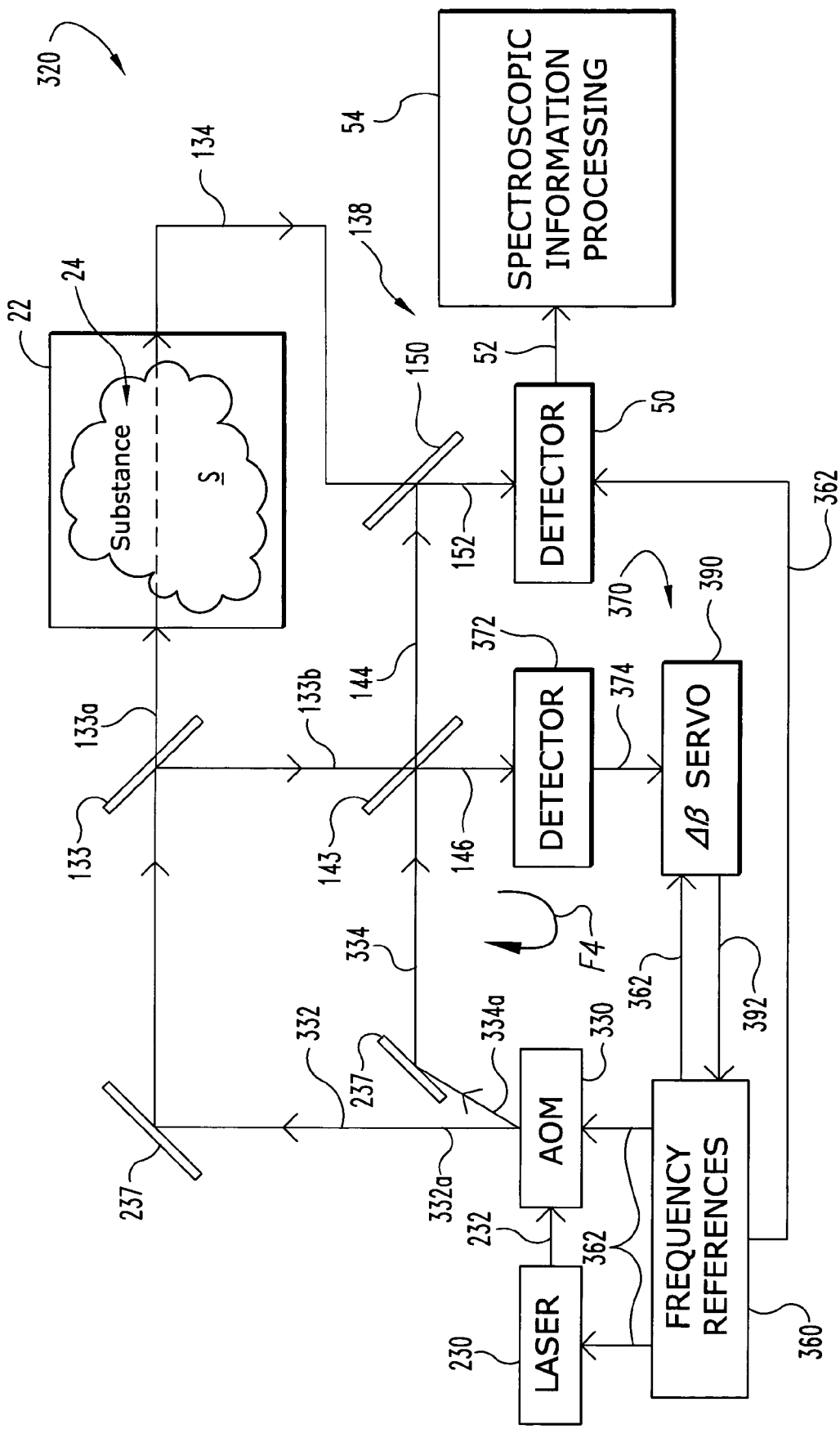
FIG. 4 is a diagrammatic view of a third implementation of the system of FIG. 1.
Figure 6:
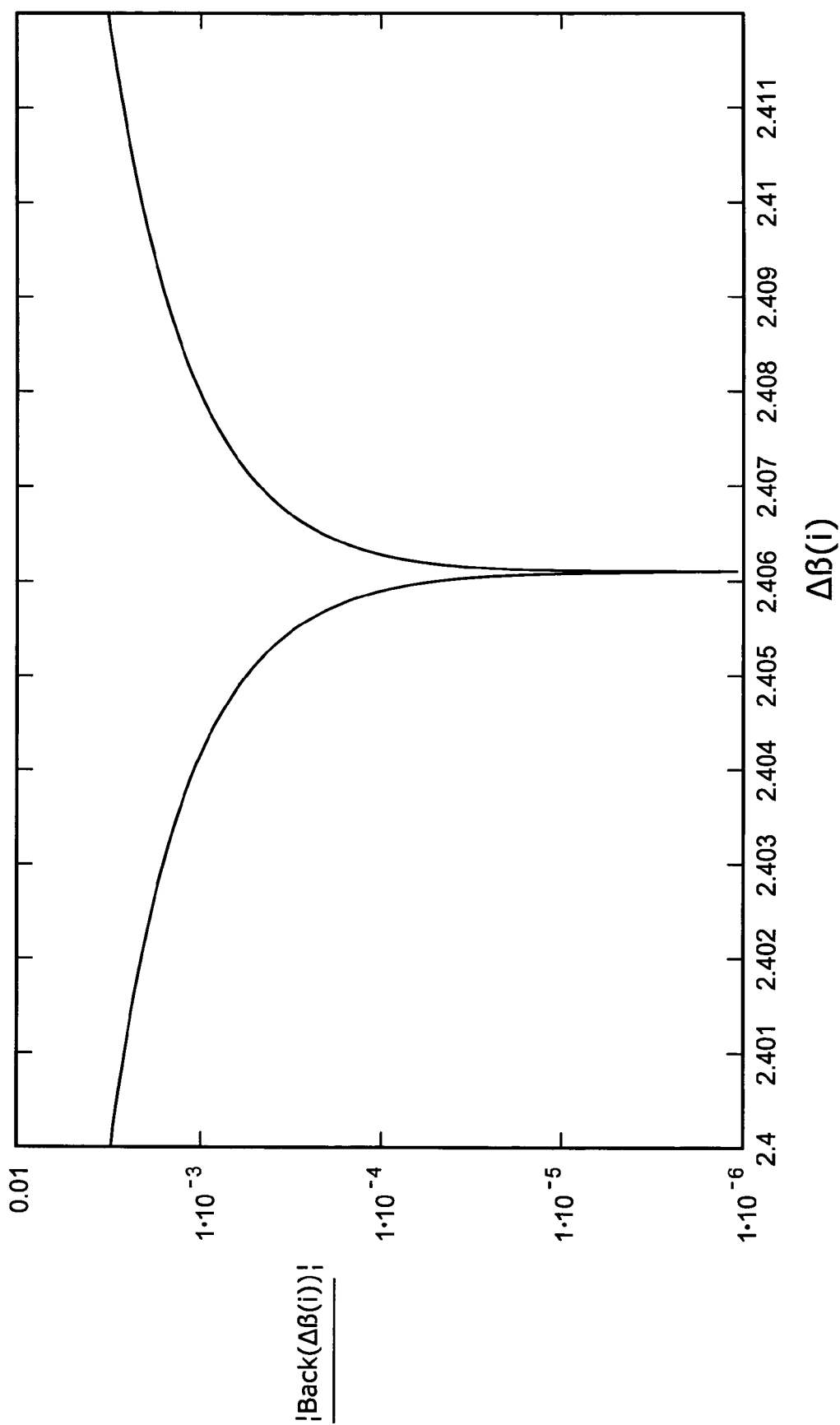

For this simulation, the absolute value, the real, and the imaginary parts of Back ($\Delta\beta$) are based on calculations on in the interval i, where: $\Delta\beta(i)=i/10$, and i ranges from 1 to 100. FIG. 6 illustrates the simulation results for the absolute value of Back ($\Delta\beta(i)$) at a greater resolution relative to FIG. 5. Specifically, for FIG. 6 $\Delta\beta(i)=i/100,000$ and i ranges from 240,000 to 241,200. These simulations show that a $\Delta\beta$ within 2.4061+/−0.0002 surpresses the background to better than $1 \times 10^{-4}$ for $M_1=0.05$ under the simulation parameters specified. The nullification of RAM at frequency $\Delta\omega$ in the detected signal is useful if it does not substantially prevent the ability to simultaneously measure absorption and dispersion. This preservation of the ability to measure absorption and dispersion while suppressing signals due to RAM has also been demonstrated by simulation. Further, it has been demonstrated by simulation that for selected $\Delta\beta$ values, RAM background nulling and preservation of the ability to measure absorption and dispersion in the detector signal occur for frequencies $|\Delta\omega+n\times\omega_m|$ where $n=\pm1, \pm2$, and $\pm3$ as well as the $n=0$ case just discussed. For any integer n, either positive or negative, there should to be selected values of $\Delta\beta$ that give RAM background nulling and preserve absorption and dispersion information. The selected values of $\Delta\beta$ that give nulling for positive n are the same as for negative n but with the signs of $\Delta\beta$ reversed. FIGS. 2–4 represent various particular, nonlimiting embodiments that implement such aspects of the present invention.

FIG. 2 depicts one implementation of the present invention in the form of spectroscopic evaluation system 120; where like reference numerals refer to like features previously described in connection with system 20. System 120 includes modulated light source subsystem 128, detection subsystem 138, and feedback subsystem 170 arranged to spectroscopically interrogate substance S in cell 22 of evaluation region 24. Subsystem 128 includes two light sources in the form of laser 130 and laser 140. Subsystem 128 also includes frequency reference and modulation control device(s) 160 that communicate various control signals via links 162, and amplifiers 164. Beam 132 from laser 130 is directed to beam splitter 133 that splits beam 132 into interrogating light 133a and feedback input light 133b. Interrogating light 133a is transmitted to substance S and is selectively attenuated by absorption/dispersion of substance S to become return/response light 134.

Laser 140 generates light beam 142. Beam 142 is directed to beam splitter 143. From splitter 143, a portion of beam 142 is transmitted to beam splitter 150, which is identified as residual amplitude addition reduction light 144. Splitter 143 also directs a portion of beam 142 to be combined with feedback input light 133b to form feedback light beam 146 that is directed to subsystem 170. Residual amplitude modulation reduction light 144 and return/response light 134 are combined with beam splitter/combiner 150 to form a corrected evaluation light 152 that is received by detection subsystem 138. Subsystem 138 includes light detector 50 that is responsive to light 152 and a control signal via one or more of links 162 to generate detector output signal 52 representative of desired spectroscopic information about substance S. Typically, detector 50 operates to phase sensitively detect signals 152 at a selected frequency such as $\Delta\omega$ or $\Delta\omega-\omega_m$. Alternatively or additionally, detection based on one or more harmonics may be utilized. Detector output signal 52 is transmitted to spectroscopic information processing device(s) 54 for further processing as desired.

Feedback subsystem 170 defines two feedback loops F1 and F2, corresponding to regulation of $\Delta\omega$ and $\Delta\beta$, respectively. Subsystem 170 includes light detector 172 that is responsive to feedback light beam 146 to generate a corresponding feedback control signal 174. Detector 172 can be of the same type as detector 50. Subsystem 170 further includes $\Delta\omega$ servo 180 and $\Delta\beta$ servo 190 that are responsive to signal 174 and control signals provided by links 162 from device(s) 160 to regulate $\Delta\omega$ and $\Delta\beta$, respectively. Servos 180 and 190 can be of a standard type used in feedback systems for the control of laser-based systems and the like. In particular, servo 180 phase-locks the difference in carrier frequencies of lasers 130 and 140 to $\Delta\omega$, adjusting operation of laser 140 as appropriate. Servo 190 mixes signal 174 with an appropriate reference frequency from device(s) 160 to maintain a desired difference in frequency modulation indices, $\Delta\beta$, selected to reduce or effectively eliminate RAM at a selected detection frequency of a detector 50 of subsystem 138. In one preferred form, where noise contributed by laser 140 is of concern, such noise can generally be reduced by utilizing a lower $\beta_2$ value relative to $\beta_1$. In still other embodiments, such aspects may not be of interest. In yet other embodiments, only one laser or other light generation device may be utilized, as provided by the nonlimiting examples depicted in FIGS. 3 and 4.

FIG. 3 presents yet another implementation of the present invention in the form of evaluation system 220; where like reference numerals refer to like features previously described in connection with system 20 and/or system 120. System 220 includes a modulated light source subsystem 228, detection subsystem 138, and feedback subsystem 270 arranged to spectroscopically interrogate substance S in cell 22 of evaluation region 24. Unlike subsystem 128, subsystem 228 is based on one laser 230. In addition to laser 230, subsystem 228 also includes Acousto-Optic Modulator (AOM) 234 and frequency reference and modulation control device(s) 260. AOM 234 is responsive to laser beam 232 from laser 230 and a frequency reference control signal from devices 260 via one or more signal communication links 262 to generate an undeflected (unmodified) light beam 236 and deflected light beam 238. Deflected light beam 238 has a carrier frequency shift $\Delta\omega$ relative to undeflected light beam 236. Accordingly, beams 236 and 238 provide different light sources designated as interrogating light source 236a and RAM correction light source 238a, respectively. Beams 236 and 238 are further directed by beam directing devices 237. Beam directing devices 237 may be any common device used for directing light, such as mirrors and/or any other beam directing component(s) as would occur to those skilled in the art.

Undeflected light beam 236 is directed to beam splitter 133. Beam splitter 133 splits beam 236 into interrogating light 133a and feedback input light 133b. Interrogating light 133a is transmitted to substance S and is selectively attenuated by absorption/dispersion of substance S to become return/response light 134.

Subsystem 228 further includes Electro-Optic Modulator (EOM) 240 that receives deflected beam 238 and outputs light beam 242. Beam 242 is directed to beam splitter 143 to provide residual amplitude modulation reduction light 144. Splitter 143 also directs a portion of beam 242 for combination with feedback input light 133b to form feedback light 146. Light 144 and light 134 is combined with splitter/combiner 150 to form corrected evaluation light 152 that has RAM reduced to improve sensitivity. Subsystem 138 includes detector 50, which receives corrected evaluation light 152 and a frequency reference control signal via one or more links 262, and produces a detector output signal 52 in response. Signal 52 includes spectroscopic information regarding substance S. Spectroscopic information processing device(s) 54 receive output signal 52 for further processing as desired.

Feedback subsystem 270 defines feedback loop F3, which corresponds to the regulation of $\Delta\beta$. Subsystem 270 includes light detector 272 that is responsive to feedback light 146 to generate a corresponding feedback control signal 274. Detector 272 can be the same type as detector 172. Subsystem 270 further includes $\Delta\beta$ servo 290 that is responsive to signal 274 and a frequency reference control signal received via one or more links 262 to generate $\Delta\beta$ regulation signal 292. Servo 290 mixes signal 274 with the reference frequency from device(s) 260 to maintain a desired difference in frequency modulation indices, $\Delta\beta$, selected to reduce or effectively eliminate RAM at a selected detection frequency at detector 50 of subsystem 138.

Referring now to FIG. 4, evaluation system 320 of another implementation of the present invention is depicted; where like reference numerals designate like features previously described in connection with system 20, 120, and/or 220. System 320 includes modulated light source subsystem 328, detection subsystem 138, and feedback subsystem 370. Subsystem 328 includes laser 230, AOM 330, and reference frequency/modulation control device(s) 360. Laser 230 outputs laser beam 232 that is received by AOM 330. From AOM 330, undeflected light beam 332 and deflected light beam 334 are transmitted. By operation of AOM 330, deflected light beam 334 has its carrier frequency $\omega_{c2}$ and modulation index $\beta_2$ shifted relative to undeflected light beam 332 by $\Delta\omega$ and $\Delta\beta$, respectively. AOM 330 controls $\Delta\omega$ and $\Delta\beta$ in response to control signals received via one or more signal communication links 362 from device(s) 360. Beams 332 and 334 are alternatively designated interrogation light source 332a and RAM correction light source 334a in FIG. 4. Undeflected laser beam 332 is directed by directing device 237 to beam splitter 133. Beam splitter 133 splits undeflected laser beam 332 into interrogating light 133a and feedback input light 133b. Interrogating light 133a is transmitted to substance S and is selectively attenuated by absorption/dispersion of substance S to become return/response light 134.

Deflected laser beam 334 is directed by directing device 237 to beam splitter 143. Beam splitter 143 provides residual amplitude modulation reduction light 144, which is combined with return/response light 134 at beam splitter/combiner 150 to form corrected evaluation light 152. Beam splitter 143 also directs a portion of beam 334 for combination with feedback input light 133b to form feedback light 146. Subsystem 138 includes light detector 50, which receives corrected evaluation light 152 and reference frequency signals via one or more links 362 from device(s) 360. Detector 50 responds to evaluation light 152 by generating a corresponding detector output signal 52. Detector output signal 52 is received by spectroscopic information processing device(s) 54 for further processing of spectroscopic information, as desired.

Feedback subsystem 370 defines feedback loop F4, which regulates $\Delta\beta$. Subsystem 370 includes light detector 372 and $\Delta\beta$ servo 390. Detector 372 generates feedback signal 374 representative of feedback light 146. Detector 372 can be of the same type as detector 50. Servo 390 receives feedback signal 374 from detector 372 and correspondingly adjusts $\Delta\beta$ via one or more signals from links 362 to device(s) 360. In one form, AOM 330 is frequency modulated to provide $\Delta\omega$ by device(s) 360 and the depth of the frequency modulation is controlled by servo 390 via device(s) 360; where the input to AOM 330 varies as $\cos(\Delta\omega^*t+A^*\sin(\omega_m^*t))$. This input signal is more complex than a pure sinusoid as is typically input for AOM 234 of system 220.

The teachings of the present invention can be utilized in a number of different modulation approaches, including single and multi-tone heterodyning, optical heterodyne mixing systems, optical resonator systems and the like to reduce RAM. As an optical heterodyne application, it should be appreciated that the return/response signal from the substance under investigation is boosted above the noise level at the detector by providing the correction light to the detector at a sufficient power level. As used herein, "frequency modulation" and "frequency-modulated" include modulation techniques that vary by phase shift on the order of 360° ($2\pi$ radians) or less (sometimes called phase modulation) as well as those resulting in frequency changes or phase changes of 360° ($2\pi$ radians) or more. Further, it is envisioned that the techniques of the present invention could be applied to frequency-modulated electromagnetic radiation with a wavelength outside the spectral range traditionally considered to define light (infrared, visible, ultraviolet), such as x-rays, to name one nonlimiting example. Further, in other embodiments, the implementations and embodiments described in connection with systems 20, 120, 220, and/or 320 can be combined or modified as would occur to those skilled in the art. In still other embodiments, RAM reduction by utilizing a $\Delta\beta$ can be provided without feedback, such that an open-loop, preset, value, and/or feedforward type of arrangement is alternatively utilized, just to name a few alternatives. For such non-feedback systems, a second detector and/or other feedback element need not be included. In yet other embodiments, feedback may be combined with feedforward and/or other control techniques as would occur to those skilled in the art.

Further, any theory, mechanism of operation, proof, or finding stated herein is meant to further enhance understanding of the present invention, and is not intended to limit the present invention in any way to such theory, mechanism of operation, proof, or finding. While the invention has been illustrated and described in detail in the drawings and foregoing description, the same is to be considered as illustrative and not restrictive in character, it being understood that only selected embodiments have been shown and described and that all equivalents, changes, and modifications that come within the spirit of the inventions as defined herein or by the following claims are desired to be protected.

What is claimed is:

1. A method, comprising:
   providing a first frequency-modulated light signal having a first modulation index;
   providing a second frequency-modulated light signal having a second modulation index;

controlling a difference between the first modulation index and the second modulation index;
combining the first frequency-modulated light signal and the second frequency-modulated light signal to reduce residual amplitude modulation in accordance with the difference;
processing at least a portion of the combined light signals; and
storing results of the processing.

2. The method of claim 1, which includes generating the first frequency-modulated light signal and the second frequency-modulated light signal from the same laser light source.

3. The method of claim 1, wherein the first frequency-modulated light signal and the second frequency-modulated light signal have a common modulation frequency and different carrier frequencies.

4. The method of claim 1, which includes directing frequency-modulated light to a substance to obtain spectroscopic information, the first frequency-modulated light signal being received from the substance as a substance-altered form of the frequency-modulated light.

5. The method of claim 4, wherein the first frequency-modulated light signal carries the spectroscopic information with the residual amplitude modulation, and wherein the processing comprises:
detecting a combination of the first frequency-modulated light signal and the second frequency-modulated light signal; and
generating an output signal based on said detecting, the output signal being representative of the spectroscopic information with the residual amplitude modulation reduced.

6. The method of claim 4, wherein said controlling includes:
detecting the first frequency-modulated light and the second frequency-modulated light signal;
generating a feedback signal based on said detecting; and
regulating generation of the second frequency-modulated light signal from an output device responsive to the feedback signal.

7. The method of claim 6, wherein the first frequency-modulated light signal and the second frequency-modulated light signal have a common modulation frequency, the second frequency-modulation index is smaller than the first modulation index, and the first frequency-modulated light signal carries the spectroscopic information with the residual amplitude modulation, wherein the processing comprises:
detecting a combination of the first frequency-modulated light signal and the second frequency-modulated light signal; and
generating an output signal based on said detecting, the output signal being representative of the spectroscopic information with the residual amplitude modulation reduced.

8. A method, comprising:
providing frequency-modulated light carrying information with undesired amplitude modulation, the frequency-modulated light being provided with a first modulation index;
generating other light that is frequency-modulated with a second modulation index, the other light having a carrier frequency different than the frequency-modulated light;
at least partially nulling the undesired amplitude modulation with the other light to improve detection of the information, wherein the first modulation index is larger than the second modulation index;
detecting at least a portion of the at least partially nulled light signal to produce a detector signal;
processing the detector signal; and
storing results of the Processing.

9. The method of claim 8, wherein the information corresponds to one or more spectroscopic characteristics of a material from which the frequency-modulated light is received.

10. The method of claim 8, which includes generating the frequency-modulated light and the other light from the same laser light source.

11. The method of claim 8, wherein the frequency-modulated light and the other light have a common modulation frequency.

12. The method of claim 8, wherein said at least partially nulling includes combining the frequency-modulated light and the other light.

13. The method of claim 8, which includes providing feedback as a function of a difference between the first modulation index and the second modulation index to regulate generation of the other light.

14. An apparatus, comprising:
a modulated light source subsystem to provide a first frequency-modulated light with a first modulation index and a second frequency-modulated light with a second modulation index;
an evaluation region to receive a substance for evaluation and direct the first light signal to the substance, the first light signal being altered by the substance when received in the region to provide a third frequency-modulated light signal carrying spectroscopic information about the substance and residual amplitude modulation; and
a first detector responsive to the second light signal and a third light signal to provide an output representative of the spectroscopic information with the residual amplitude modulation reduced in accordance with a difference between the first modulation index and the second modulation index.

15. The apparatus of claim 14, further comprising a feedback device responsive to the first light signal and the second light signal to control the difference between a first modulation index and the second modulation index.

16. The apparatus of claim 15, further comprising a second detector operable to detect a combination of the first light signal and the second light signal, the first light detector being coupled to the feedback device.

17. The apparatus of claim 16, further comprising:
a first beam splitter to direct the first light signal to both the first detector and the interrogation region; and
a second beam splitter to direct the second light signal to both the first detector and the second detector.

18. The apparatus of claim 14, wherein the modulated light source subsystem includes at least one laser.

19. The apparatus of claim 18, wherein the modulated light source subsystem includes at least one of an acousto-optic modulator and an electro-optic modulator.

20. The apparatus of claim 14, wherein the modulated light source subsystem includes at least two lasers.

21. The apparatus of claim 20, further comprising a servo device to maintain a carrier frequency difference between the first light signal and the second light signal.

22. The apparatus of claim 14, wherein the modulated light source subsystem is operable to provide the first modulation index at a higher value than the second modulation index.

23. An apparatus, comprising:
- means for interrogating a material to provide a first frequency-modulated light signal having a first modulation index, the first frequency-modulated light carrying spectroscopic information with residual amplitude modulation;
- means for generating a second frequency-modulated light signal having a second modulation index;
- means for combining the first frequency-modulated light signal and the second frequency-modulated light signal;
- means for reducing the residual amplitude modulation in accordance with a difference between the first modulation index and the second modulation index to improve detection of the spectroscopic information;
- means for detecting the spectroscopic information;
- means for processing the spectroscopic information; and
- means for storing results of the processing.

24. The method of claim 1, wherein processing at least a portion of the combined light signals comprises detecting at least a portion of the combined light signals.

25. The method of claim 1, wherein one or more of the following are performed before or after processing at least a portion of the combined light signals:
- analyzing spectroscopic information;
- outputting spectroscopic information;
- displaying spectroscopic information;
- indicating spectroscopic information;
- storing spectroscopic information; and
- transmitting spectroscopic information.

* * * * *

UNITED STATES PATENT AND TRADEMARK OFFICE
CERTIFICATE OF CORRECTION

PATENT NO. : 7,230,712 B2
APPLICATION NO. : 10/700161
DATED : June 12, 2007
INVENTOR(S) : Bret D. Cannon It is certified that error appears in the above-identified patent and that said Letters Patent is hereby corrected as shown below:

In the Specification:

Column 4, line 17, "(where: $\Delta\beta=\beta_2-\beta_1$) Feedback", should read --(where: $\Delta\beta=\beta_2-\beta_1$). Feedback--

Column 5, line 21, "utilize respect", should read --utilized with respect--

Column 5, line 37, "magnitud determined", should read --magnitude; and $r_2(s, \beta_2)$ is determined--

Column 6, line 23, " $\left(\frac{-\alpha_0^2 d}{2}\right)$ " should read -- $\left(\frac{-\alpha 0^2 d}{2}\right)$ --

Column 6, line 31, " $b_k^t \overline{\alpha_{kp}^t}$ " should read -- $b_k^* \overline{\alpha_{kp}^*}$ --

Column 12, line 6, "Processing.", should read --processing.--

Signed and Sealed this
Fourteenth Day of May, 2013

Teresa Stanek Rea
*Acting Director of the United States Patent and Trademark Office*